(12) United States Patent
Fine et al.

(10) Patent No.: US 8,646,445 B2
(45) Date of Patent: Feb. 11, 2014

(54) NITRIC OXIDE DELIVERY SYSTEM

(75) Inventors: David H. Fine, Cocoa Beach, FL (US); Gregory Vasquez, Cocoa, FL (US); Bryan Johnson, Orlando, FL (US); Jody Fuller, Merritt Island, FL (US); Ryan Denton, Titusville, FL (US)

(73) Assignee: Geno LLC, Cocoa, FL (US)

( * ) Notice: Subject to any disclaimer, the term of this patent is extended or adjusted under 35 U.S.C. 154(b) by 0 days.

(21) Appl. No.: 12/951,811

(22) Filed: Nov. 22, 2010

(65) Prior Publication Data

US 2011/0220103 A1    Sep. 15, 2011

Related U.S. Application Data

(60) Provisional application No. 61/263,332, filed on Nov. 20, 2009.

(51) Int. Cl.
*A61M 16/10* (2006.01)
*A61M 16/00* (2006.01)
*H05B 3/00* (2006.01)

(52) U.S. Cl.
USPC ............ 128/202.26; 128/200.24; 128/203.12; 128/203.26; 128/204.17

(58) Field of Classification Search
USPC ............ 128/202.26, 203.12, 205.27, 204.17, 128/203.26, 203.27; 423/210, 235, 239.1, 423/239.2; 141/2, 3, 20, 31, 85; 96/139, 96/152; 55/325, 518; 604/13, 23, 24, 27; 422/213, 216
See application file for complete search history.

(56) References Cited

U.S. PATENT DOCUMENTS

| | | | |
|---|---|---|---|
| 1,021,234 A | | 3/1912 | Von Bemeck |
| 1,934,968 A | * | 11/1933 | Connolly ............ 208/299 |
| 2,272,810 A | | 2/1942 | Denys |
| 2,622,593 A | * | 12/1952 | Peirano ............ 128/200.18 |
| 3,085,862 A | * | 4/1963 | Atadan et al. ............ 423/386 |
| 3,566,867 A | * | 3/1971 | Dryden ............ 128/205.28 |
| 3,695,289 A | * | 10/1972 | Capdevielle et al. ......... 137/375 |
| 3,738,360 A | * | 6/1973 | Dryden ............ 128/205.28 |
| 3,930,813 A | | 1/1976 | Gessner |
| 4,010,897 A | | 3/1977 | Treharne |
| 4,201,695 A | | 5/1980 | Juntgen et al. |
| 4,270,933 A | | 6/1981 | Meny et al. |
| 4,287,040 A | | 9/1981 | Alamaro |
| 4,399,942 A | | 8/1983 | Chand |
| 4,714,486 A | * | 12/1987 | Silverthorn ............ 96/134 |
| 4,774,069 A | | 9/1988 | Handley |

(Continued)

FOREIGN PATENT DOCUMENTS

| | | |
|---|---|---|
| WO | WO 94/16740 | 8/1994 |
| WO | WO 95/07610 | 3/1995 |
| WO | WO 01/15738 | 3/2001 |

OTHER PUBLICATIONS

Cooney et al., "Products of γ-tocopherol with NO2 and their formation in rat insulinoma (RINm5F) cells," Free Radical Biology and Medicine, vol. 19, Issue 3, Sep. 1995, p. 259-269.

(Continued)

*Primary Examiner* — Justine Yu
*Assistant Examiner* — Douglas Sul
(74) *Attorney, Agent, or Firm* — Steptoe & Johnson LLP

(57) ABSTRACT

An ambulatory or stationary device for delivery of a therapeutic amount of nitric oxide to an individual's lungs.

38 Claims, 9 Drawing Sheets

(56) References Cited

U.S. PATENT DOCUMENTS

| | | | |
|---|---|---|---|
| 4,778,450 A | | 10/1988 | Kamen |
| 4,859,116 A | * | 8/1989 | Harris ........................... 405/52 |
| 4,936,705 A | * | 6/1990 | Schneider ..................... 405/54 |
| 4,963,327 A | | 10/1990 | Russell |
| 5,156,334 A | * | 10/1992 | Kimbell et al. ................. 239/6 |
| 5,228,434 A | | 7/1993 | Fishman |
| 5,324,478 A | * | 6/1994 | Mermoud et al. .............. 422/62 |
| 5,396,882 A | | 3/1995 | Zapol |
| 5,485,827 A | | 1/1996 | Zapol |
| 5,514,204 A | | 5/1996 | Sheu et al. |
| 5,514,205 A | * | 5/1996 | Awaji ............................. 96/152 |
| 5,525,357 A | | 6/1996 | Keefer |
| 5,545,614 A | | 8/1996 | Stamler |
| 5,558,083 A | | 9/1996 | Bathe |
| 5,570,683 A | | 11/1996 | Zapol |
| 5,615,669 A | | 4/1997 | Olsson |
| 5,647,354 A | | 7/1997 | Lakhani et al. |
| 5,651,358 A | | 7/1997 | Briend |
| 5,676,963 A | | 10/1997 | Keefer |
| 5,683,668 A | | 11/1997 | Hrabie |
| 5,692,495 A | | 12/1997 | Sheu |
| 5,743,251 A | * | 4/1998 | Howell et al. ............ 128/200.14 |
| 5,823,180 A | | 10/1998 | Zapol |
| 5,827,420 A | | 10/1998 | Shirazi |
| 5,839,433 A | | 11/1998 | Higenbottam |
| 5,846,297 A | | 12/1998 | Schleicher et al. |
| 5,871,009 A | | 2/1999 | Rydgren |
| 5,873,359 A | | 2/1999 | Zapol |
| 5,882,385 A | * | 3/1999 | Bosquain et al. ............... 96/138 |
| 5,994,444 A | | 11/1999 | Trescony |
| 6,046,383 A | | 4/2000 | Elsenga-Boersma et al. |
| 6,083,399 A | * | 7/2000 | Jameson et al. .............. 210/634 |
| 6,103,275 A | | 8/2000 | Seitz et al. |
| 6,109,260 A | | 8/2000 | Bathe |
| 6,158,434 A | | 12/2000 | Lugtigheid et al. |
| 6,190,704 B1 | | 2/2001 | Murrell |
| 6,261,594 B1 | | 7/2001 | Smith |
| 6,270,779 B1 | | 8/2001 | Fitzhugh |
| 6,576,044 B1 | | 6/2003 | Ho et al. |
| 6,635,273 B1 | | 10/2003 | Loscalzo et al. |
| 6,749,834 B2 | | 6/2004 | Fein et al. |
| 6,758,214 B2 | | 7/2004 | Fine et al. |
| 6,766,220 B2 | * | 7/2004 | McRae et al. .................. 700/266 |
| 6,896,899 B2 | | 5/2005 | Demopolos et al. |
| 7,025,869 B2 | | 4/2006 | Fine et al. |
| 7,040,313 B2 | | 5/2006 | Fine et al. |
| 7,282,519 B2 | | 10/2007 | Garvey et al. |
| 7,288,664 B2 | | 10/2007 | Kleiner |
| 7,618,594 B2 | | 11/2009 | Rounbehler et al. |
| 2001/0012851 A1 | | 8/2001 | Lundy |
| 2002/0090401 A1 | | 7/2002 | Tucker et al. |
| 2002/0092363 A1 | * | 7/2002 | Jorgenson et al. ......... 73/861.95 |
| 2003/0140924 A1 | * | 7/2003 | Aylsworth et al. ....... 128/204.26 |
| 2005/0142218 A1 | | 6/2005 | Tucker et al. |
| 2006/0048779 A1 | * | 3/2006 | Rounbehler et al. ..... 128/203.12 |
| 2006/0096596 A1 | * | 5/2006 | Occhialini et al. ....... 128/204.18 |
| 2006/0207594 A1 | * | 9/2006 | Stenzler et al. .......... 128/204.18 |
| 2009/0285731 A1 | | 11/2009 | Rounbehler et al. |

OTHER PUBLICATIONS

Licht, W.R. et al., "Use of Ascorbic Acid to Inhibit Nitrosation: Kinetic and Mass Transfer Considerations for an In Vitro System," Carcinogenesis, IRL Press At Oxford University Press, Oxford, Mar. 1988, pp. 365-371.

Mascarenhas, Oscar Carlton, "Epoxy-Based Medical Grade Adhesive Hydrogels and Nitric Oxide Releasing Polymers", Dissertation Abstracts International, vol. 55/02-B, pp. 445 (1993).

Material Safety Data Sheet, Silica gel, grade 41, 3-8 mesh MSDS (created Oct. 9, 2005).

Pulfer, Sharon Kay, "Nitric Oxide Releasing Polymers and Their Application to Vascular Devices (Polyethyleneimine, Polytetrafluoroethylene)", Dissertaion Abstracts International, vol. 56/12-B, pp. 6727 (1995).

Roselle, Dominick C., et al., "Characterization and Nitric Oxide Release Studies of Lipophilic 1-Substituted Diazen-1-ium,1,2-Diolates", Journal of Controlled Release, vol. 51, pp. 131-142 (1998).

Smith, Daniel J.,et al., "Nitric Oxide-Releasing Polymers Containing the [N(O)NO] Group", Journal of Medicinal Chemistry, vol. 39, No. 5, pp. 1148-1156 (1996).

Suzuki, "Nitrogen Oxides Generation Method for Recovered Nitric Acid by Electrolysis. An Action Plan for Reduction of Low-Level-Liquid-Waste in Processing Plant," Kyoto Daigaku Genshiro Jikkensho, (Tech. Rep.) 1991, Kurri-Ter-361, pp. 19-26.

Taira, Masafumi, et al. "Continuous Generation System for Low-Concentration Gaseous Nitrous Acid", Analytical Chemistry, vol. 62, No. 6, pp. 630-633, (1990). cited by other . International Search Report, 8 pages, Mar. 10, 2004.

Tannenbaum, S.R. et al., "Inhibition of Nitrosamine Formation by Ascorbic Acid," The American Journal of Clinical Nutrition, American Society of Clinical Nutrition, Bethesda, Maryland, Jan. 1991, vol. 53, pp. 247-250.

International Preliminary Report on Patentability dated May 31, 2012 for PCT/US2010/057629.

* cited by examiner

NITRIC OXIDE DELIVERY SYSTEM

CLAIM OF PRIORITY

This application claims the benefit of prior U.S. Provisional Application No. 61/263,332, filed on Nov. 20, 2009, which is incorporated by reference in its entirety.

TECHNICAL FIELD

This description relates to ambulatory and stationary devices for the delivery of nitric oxide.

BACKGROUND

Nitric oxide (NO), also known as nitrosyl radical, is a free radical that is an important signaling molecule. For example, NO causes smooth muscles in blood vessels to relax, thereby resulting in vasodilation and increased blood flow through the blood vessel. These effects are limited to small biological regions since NO is highly reactive with a lifetime of a few seconds and is quickly metabolized in the body.

Typically, NO gas is supplied in a bottled gaseous form diluted in nitrogen gas ($N_2$). Great care has to be taken to prevent the presence of even trace amounts of oxygen ($O_2$) in the tank of NO gas because NO, in the presence of $O_2$, is oxidized into nitrogen dioxide ($NO_2$). Unlike NO, the part per million levels of $NO_2$ gas is highly toxic if inhaled and can form nitric and nitrous acid in the lungs.

SUMMARY

In one embodiment, a system for delivering a therapeutic amount of nitric oxide includes a liquid reservoir containing dinitrogen tetroxide, a tube coupled to the reservoir, a first ribbed tube coupled to the tube; wherein the tube includes a surface-active material coated with a reducing agent and a patient interface coupled to the first ribbed tube, wherein the tube converts nitrogen dioxide into nitric oxide prior to reaching the patient interface. The tube can be a quartz tube or a silica tube. The tube can be any compatible material that can have a bore size of about 50 microns or less. The tube can have a bore size of about 25 microns or less. The tube can have a bore size of 10 microns or less. The tube can be sealed. The system is activated by braking off the tip of the sealed tube. The tube can be quartz. The system can further include a valve coupled to the reservoir and the tube, wherein the valve can act as a variable sized hole. The system can further include an air pump in communication with the reservoir. The pump can be a battery-driven pump. The system can further include a source of pressurized inhalable gas such as air or oxygen. The system can further include a heating element associated with the reservoir. The patient interface can be a mouth piece, nasal cannula, face mask, fully-sealed face mask, or an endotracheal tube attached to a ventilator or anesthesia machine. In certain embodiments, the reservoir can contain compressed nitrogen dioxide with or without a diluent gas, for example, the reservoir can further include nitrogen, air, oxygen-enriched air, or substantially pure oxygen. The surface-active material can be a silica gel. The antioxidant can be ascorbic acid, alpha tocopherol, or gamma tocopherol. The antioxidant can be any antioxidant that is capable of reducing nitrogen dioxide to nitric oxide, even if the yield is very low. The surface active material should have a very large effective surface area to allow for multiple collisions so that even a 50% yield at each site leads to 99.99% effective yield when the process is repeated many thousands of times The system can further include a second ribbed tube including a surface-active material saturated with a reducing agent. Any appropriate reducing agent that can convert $NO_2$ or $N_2O_4$ to NO can be used as determined by a person of skill in the art. For example, the reducing agent can include a hydroquinone, glutathione, and/or one or more reduced metal salts such as Fe(II), Mo(VI), NaI, Ti(III) or Cr(III), thiols, or $NO_2^-$. The reducing agent can be an antioxidant. The antioxidant can be an aqueous solution of an antioxidant. The antioxidant can be ascorbic acid, alpha tocopherol, or gamma tocopherol. Any appropriate antioxidant can be used depending on the activities and properties as determined by a person of skill in the art. The antioxidant can be used dry or wet. The patient interface can be a delivery tube to the patient's mouth or nose or to a tube in the throat, or to a ventilator or anesthesia machine that delivers gas to a patient. The system can be adapted to be worn on a patient's body.

The reservoir can be spherical or cylindrical. The reservoir can be a fused silica reservoir. The reservoir can be a non-reactive metal reservoir. The non-reactive metal can include palladium, silver, platinum, gold, aluminium or stainless steel. The reservoir can be an aluminium reservoir or a stainless steel reservoir. The system can further include an insulation covering the reservoir and the tube. The insulation covering can further include an alkaline solution. The insulation can be activated charcoal which absorbs $NO_2$ which can also serve as a safety measure in case of catastrophic failure of the system. The alkaline solution can be calcium oxide, sodium hydroxide, sodium carbonate, potassium hydroxide, ammonium hydroxide or sodium silicate.

In another embodiment, a device for delivering nitric oxide to a patient can include a liquid reservoir containing dinitrogen tetroxide, a tube coupled to the reservoir, wherein tube has a bore size of about 25 microns more or less, a first ribbed tube including a surface-active material saturated with an aqueous solution of an antioxidant, that is coupled to the tube and a patient interface coupled to the first ribbed tube, wherein the first ribbed tube converts nitrogen dioxide into nitric oxide prior to reaching the patient interface. The device can further include a heating element associated with the reservoir. The device can also include an air pump in communication with the reservoir. The pump can be a battery-driven pump. The device can further include a nitric oxide and or a nitrogen dioxide monitor. The monitor can be a conventional monitor that withdraws the gaseous sample from the flow to the patient and delivers it to the detector by means of a sampling tube. The monitor can also be mounted in line with the gas plumbing going to the patient so that it is part of the side wall of the tubing. The advantage of such an inline monitor is that the output is very fast, and that there is no need for a sample line and no need to correct the output for the formation of nitrogen dioxide (and loss of nitric oxide) in the tubing to the monitor.

In a further embodiment, a hollow tube including a body having a first end and a second end, wherein the body includes multiple concentric hollow ribs and contains a surface-active material. The surface-active material can be saturated with an aqueous solution of an antioxidant to convert nitrogen dioxide into nitric oxide. The surface-active material can include a silica gel, activated charcoal, activated carbon, activated alumina or calcium sulfate.

Other features will become apparent from the following detailed description, taken in conjunction with the accompanying drawings, which illustrate by way of example, the features of the various embodiments.

DETAILED DESCRIPTION

Figure 1:
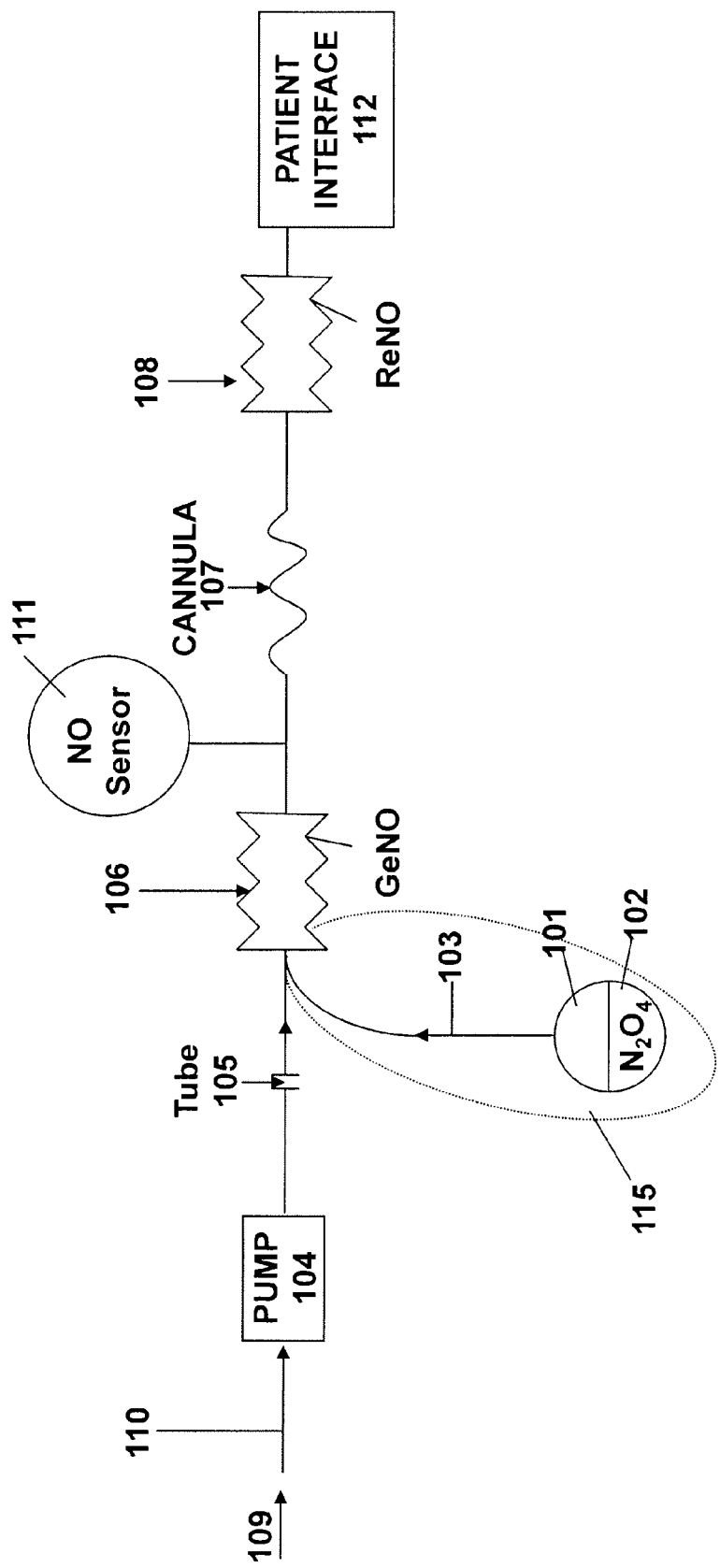
FIG. 1 is a diagram of a NO delivery system.

Nitric oxide (NO), also known as nitrosyl radical, is a free radical that is an important signaling molecule in pulmonary vessels. Nitric oxide (NO) can moderate pulmonary hypertension caused by elevation of the pulmonary arterial pressure. Inhaling low concentrations of nitric oxide (NO), for example, in the range of 1-100 ppm can rapidly and safely decrease pulmonary hypertension in a mammal by vasodilation of pulmonary vessels.

Some disorders or physiological conditions can be mediated by inhalation of nitric oxide (NO). The use of low concentrations of inhaled nitric oxide (NO) can prevent, reverse, or limit the progression of disorders which can include, but are not limited to, acute pulmonary vasoconstriction, traumatic injury, aspiration or inhalation injury, fat embolism in the lung, acidosis, inflammation of the lung, adult respiratory distress syndrome, acute pulmonary edema, acute mountain sickness, post cardiac surgery acute pulmonary hypertension, persistent pulmonary hypertension of a newborn, perinatal aspiration syndrome, haline membrane disease, acute pulmonary thromboembolism, heparin-protamine reactions, sepsis, asthma and status asthmaticus or hypoxia. Nitric oxide (NO) can also be used to treat chronic pulmonary hypertension, bronchopulmonary dysplasia, chronic pulmonary thromboembolism and idiopathic or primary pulmonary hypertension or chronic hypoxia. NO can also be used to treat influenza. NO can further be used to inhibit the replication of the influenza virus in the lungs.

Generally, nitric oxide (NO) is inhaled or otherwise delivered to the individual's lungs. Providing a therapeutic dose of NO would treat a patient suffering from a disorder or physiological condition that can be mediated by inhalation of NO or supplement or minimize the need for traditional treatments in such disorders or physiological conditions.

Currently, approved devices and methods for delivering inhaled NO gas require complex and heavy equipment. NO gas is stored in heavy gas bottles with nitrogen and no traces of oxygen. The NO gas is mixed with air or oxygen with specialized injectors and complex ventilators, and the mixing process is monitored with equipment having sensitive microprocessors and electronics. All this equipment is required in order to ensure that NO is not oxidized into nitrogen dioxide ($NO_2$) during the mixing process since $NO_2$ is highly toxic. However, this equipment is not conducive to use in a non-medical facility setting (e.g., combat operations, remote wilderness, at home, while shopping or at work) since the size, cost, complexity, and safety issues restrict the operation of this equipment to highly-trained professionals in a medical facility.

NO treatment is effective, but a patient's mobility may be limited since the treatment requires bulky and/or heavy equipment. Accordingly, a light, portable, ambulatory device for delivering NO with air has the potential to improve a patient's quality of life. The device may be powered by a small, battery-driven pump or by patient inhalation (similar to smoking a cigar). Additionally, a treatment providing NO (e.g., converting $N_2O_4$ into NO) may be more cost effective than oxygen therapy.

The delivery devices disclosed herein are self-contained, portable systems that do not require heavy gas bottles, gas pressure and flow regulators, sophisticated electronics, or monitoring equipment. Additionally, the delivery devices are easy to use and do not require any specialized training. Moreover, the delivery devices allow an individual to self-administer a NO treatment. The delivery devices are also lightweight, compact, and portable. According to one embodiment, the NO delivery device is the size of a coke can for one-time use or short-term treatments lasting from 24 to 200 hours. Alternatively, the treatments can last from 5 to 20 minutes in a catheterization laboratory, to 6 hours during the day, to 24 hours per day to weeks at a time. In another embodiment, the NO delivery device is the size of a cigar or a conventional inhaler. Alternatively, the NO delivery device is a larger device, yet portable device that can deliver NO for longer periods of time. In one embodiment, the NO delivery device can deliver NO for 4 days at 80 ppm NO and a flow rate of 1 L/min from a source of only 1 gram of liquid $N_2O_4$ or less than 0.7 mL of $N_2O_4$. In another embodiment, the NO delivery device can deliver NO for several days from a source of only 0.5 gram of liquid $N_2O_4$.

As shown in FIG. 1, the NO delivery system includes reservoir 101. Generally, the reservoir 101 supplies NO lasting a few minutes to one or more days of continuous use, depending upon the method of storing the NO. In one embodiment, the reservoir 101 stores a therapeutic amount of $NO_2$ that is converted into NO. The therapeutic amount of NO is diluted to the necessary concentration while it is still $NO_2$, before the $NO_2$ is converted into NO. In another embodiment for long-term use for many days, the NO is stored as liquid dinitrogen tetraoxide ($N_2O_4$) that is vaporizable into $NO_2$, typically, which in turn, is converted into NO. In various embodiments, the reservoir 101 is sized to hold a few milligrams to tens of grams of liquid $N_2O_4$. For short-term treatments, the reservoir 101 can be sized to contain a few milligrams of $N_2O_4$. For example, the reservoir 101 may be sized to hold approximately 7 mg of $N_2O_4$ (1), which would provide 20 ppm of NO for ten minutes. For long-term applications, the reservoir 101 may be sized to contain 10 or more grams of $N_2O_4$ for long-term use such as several weeks. For example, a reservoir containing approximately 0.3 g of $N_2O_4$ may provide 20 ppm of NO at 20 L/min. for 24 hours, and a reservoir containing 10 g of $N_2O_4$ would provide a continuous supply of NO for approximately 30 days. In other examples, the reservoir 101 is sized to hold less then than 1 ml, 2 ml, 3 ml, 4 ml, 5 ml or 10 ml of liquid $N_2O_4$.

In one embodiment, the reservoir 101 can contain 1 g (about 0.7 ml) of $N_2O_4$ (102). The reservoir 101 can be attached to a tiny orifice or tube 103 with a very narrow bore. The reservoir 101 and the tube 103 can be covered by insulation 115. Since $N_2O_4$ boils at 21° C., the pressure inside the reservoir would be approximately 15 psi at 31° C., 30 psi at 41° C. and 60 psi at 51° C. for example. Instead of a gas regulator to control the pressure of the gas within a device, the temperature can be controlled such that the pressure inside the device is controlled precisely. As the gas vaporizes, one molecule of $N_2O_4$ forms two molecules of $NO_2$. Using the known physical gas properties of $NO_2$, a critical orifice hole of about 3 to 4 microns would leak out $NO_2$ at about 0.16 ml per minute. If this 0.16 ml of $NO_2$ were diluted into a gas stream of 2 liters per minute, the resulting concentration would be 80 ppm (parts per million). The same result can be achieved by using for example, a quartz tube 103 with a 25 micron diameter bore size and about 20 inches long.

The pressure inside the reservoir 101 can be controlled very precisely by controlling the temperature. The flow rate Q out of the reservoir is proportional to the differential pressure $\Delta P$, the fourth power of the diameter of the tube $D^4$, and inversely proportional to the length of the tube. This equation was tested for this application:

$$Q = \frac{\Pi \Delta P D^4}{128 \mu L}$$

In one embodiment, a small ON/OFF valve can be inserted between the reservoir and the fine tube. The valve can act as a variable sized hole. In another embodiment, the quartz tube can be sealed off with a hot flame and have no valve; resulting in an extremely simple device with just a reservoir which is heated to a known temperature and a fine tube. The device can be activated by heating the reservoir and cutting the tube to the desired length.

In another embodiment, the NO delivery system can include an air pump 104 that blows about 0.5 to 2 L/min of air through a tube 105. In other embodiments, the air pump can operate at about 4 to 20 L/min. The heated $N_2O_4$ source can leak $NO_2$ slowly into a stream to form a concentration of about 80 ppm of $NO_2$ in air. This is then passed through a short (about 1 inch) ribbed tube 106 containing the silica gel and ascorbic acid. If the packed tube is not ribbed and has smooth walls, then the tube needs to be in the vertical position so as to prevent a path whereby the air could bypass the silica gel and ascorbic acid, to avoid settling of the fine powder.

A second back up ribbed tube 108 may be located just before the cannula 107. There are three reasons for doing so: First, the second tube can convert any $NO_2$ that is formed in the interconnecting tubing back into NO. Second, the second tube can provide a doubly redundant $NO_2$ to NO reactor, in case of failure of the first tube, 106. Third, the second tube can guarantee the absence of $NO_2$ and therefore can replace the need for having a $NO_2$ monitor for safety purposes. The safety is further enhanced when the two tubes are made from different batches of silica and ascorbic acid.

FIG. 1 illustrates the air intake (arrow 109) and air intake connection 110 to the air pump 104. The pressurized air then leaves the pump. For ambulatory use, this air flow can be in the range of 0.1 to 5 L/min. In one embodiment, the pump is a battery-driven pump. The air can also be supplied by a compressor. The air can also be supplied from a wall outlet, such as in a hospital. Oxygen can be used to replace the air, provided that the internal components of the system are suitable for use with pure oxygen. The liquid $N_2O_4$ contained in the reservoir 101 is connected to a ribbed tube 106 that contains a surface-active material containing an aqueous solution of an antioxidant, by means of a fine fused capillary tube 103. The tube can be a silica tube, a fused silica tube or a quartz tube. The tube can have a bore size of about 50 microns or less, 25 microns or less, for example, 15 microns, 10 microns or 5 microns. The tube can have a bore size of 10 microns or less. The size of the tube can be chosen based on the concentration that is needed and the flow volume. In one embodiment, to deliver 80 ppm at 20 L, a bore size of 80 microns or more may be required. The tube can be of the type that is used for gas chromatography. The tube has no interior coating and may be coated on the outside with a polyamide protective layer to prevent the tube from breaking. The tube can be 30 inches long or as little as 0.25 inches so long as the pressure drop across the tube is calculated to provide the correct amount of flux of $NO_2$ to provide the therapeutic dose. Tubing lengths of between 0.1 to 50 inches have been used.

When heated, the liquid $N_2O_4$ will vaporize to $NO_2$ since the boiling point of $N_2O_4$ is about 21° C. The vapour pressurizes the reservoir and a small amount of the gas is vaporized through the tube 103 into the first ribbed tube 106. In, or just before, the first ribbed tube 106, the $NO_2$ is first mixed with air and then converted to NO. The ribbed tube may also be referred to as a conversion cartridge or GeNOrator. In one embodiment, a NO generation cartridge, a GENO cartridge, or a GENO cylinder may be used in place of or together with the ribbed tube. Such NO generation cartridges are described in U.S. application Ser. No. 12/541,144 (herein incorporated by reference). The first ribbed tube 106 includes an inlet and an outlet. In one embodiment, the ribbed tube is filled with a surface-active material that is soaked with a solution of antioxidant in water to coat the surface-active material. This combination may sometimes be referred to as pixie dust. The antioxidant can be ascorbic acid, alpha tocopherol, or gamma tocopherol or almost any suitable reducing agent. The surface-active material can be silica gel or any material with a large surface area that is compatible with the reducing agent.

The inlet of the ribbed tube may receive the air flow having $NO_2$. The inlet can also receive an air flow with $NO_2$ in nitrogen ($N_2$), air, or oxygen ($O_2$). The conversion occurs over a wide concentration range. In one embodiment, the ribbed tube was packed with silica gel that had first been soaked in a saturated aqueous solution of ascorbic acid. Other sizes of the cartridge are also possible. The moist silica gel was prepared using ascorbic acid (i.e., vitamin C) designated as A.C.S reagent grade 99.1% pure from Aldrich Chemical Company and silica gel from Fischer Scientific International, Inc., designated as S8 32-1, 40 of Grade of 35 to 70 sized mesh. Other similar sizes of silica gel can also be effective, provided that the particular material is tested experimentally to determine whether it is suitable. The silica gel may be moistened with a solution of ascorbic acid that had been prepared by mixing from about 5% up to 35% by weight ascorbic acid in water, stirring, and straining the water/ascorbic acid mixture through the silica gel, followed by draining. It has been found that the conversion of $NO_2$ to NO proceeds well when the silica gel coated with ascorbic acid is moist. The conversion of $NO_2$ to NO does not proceed well when the $NO_2$ is bubbled through an aqueous solution of ascorbic acid alone.

NO gas can then exit from the first ribbed tube 106. In one embodiment, NO exits from the first ribbed tube 106 into a NO sensor 111. The NO sensor can be directly coupled to a nasal cannula tubing 107. The NO sensor can be an optional safety device used to assure that NO gas is flowing. The NO sensor can be a separate NO monitor, or the sensor and the electronics can be mounted in the gas flow path itself. The reason for mounting in the flow path is that there is no need for a separate sample line, and also that the response time of the detector is reduced from multiple seconds to milliseconds.

In a further embodiment, the nasal cannula tubing 107 can be connected to a second ribbed tube 108 that contains a surface-active material that is soaked with a solution of antioxidant in water to coat the surface-active material. The function of the second ribbed tube 108 is the same as the first ribbed tube 106 and serves as a back up in case the first ribbed tube fails to convert $NO_2$ to NO. The mixture then flows directly to a patient interface 112. The patient interface can be a mouth piece, nasal cannula, face mask, or fully-sealed face mask. The $NO_2$ concentration in the gas stream to the patient is always zero, even if the gas flow to the cannula is delayed, since the second ribbed tube will convert any $NO_2$ present in the gas lines to NO.

It is contemplated that one or more of the components of the system illustrated in FIG. 1 may not be directly connected together. FIG. 1 illustrates that the pump 104 and power module is separate from the $N_2O_4$ reservoir 101 and the first and second ribbed tubes 106 and 108. The power module can be purchased and assembled separately and can have its own battery charger built in or use one way or rechargeable batteries. The pump may be powered from a electrical outlet such as in a home, can be battery operated, solar powered, or crank powered. The $N_2O_4$ reservoir 101 and the first and second ribbed tubes 106 and 108 can be a disposable module. The disposable module can be purchased separately at a pharmacy for example, as a prescription drug. The disposable module can be designed to last for 6 hours, 24 hours, 2 days, 4 days, 7 days, 2 weeks, a month or longer. In one embodiment, with twice the amount of material for both $N_2O_4$ and ascorbic/silica gel combination in the ribbed tubes, the lifetime of the disposable modules can be increased by two-fold.

The system illustrated in FIG. 1 can optionally include a $NO_2$ monitor. The $NO_2$ sensor can be a separate $NO_2$ monitor, or the sensor and the electronics can be mounted in the gas flow path itself. The reason for mounting in the flow path is that there is no need for a separate sample line, and also that the response time of the detector is reduced from multiple seconds to milliseconds. For $NO_2$ it is especially important that the sample lines be kept as short as possible, since $NO_2$ "sticks" to the tubing walls and as a result the time constant of the system can be very long, for example minutes to hours. Having an inline sensor can eliminate this problem.

The NO and NO sensor can be calibrated periodically and also checked periodically to ensure that they are fully functional and have not failed and/or are still in calibration. Calibration and checking can be tedious and time consuming and there is no insurance that the calibration had failed immediately after the previous calibration. For this reason it is desirable to auto calibrate the sensors. One method which has been successful is to supply a very short time spike of NO and/or $NO_2$, such that the duration of the spike is only a few milliseconds. This is enough time to have the computer recognize the time frequency and magnitude of the spike and use the result as a calibration check.

Figure 2:
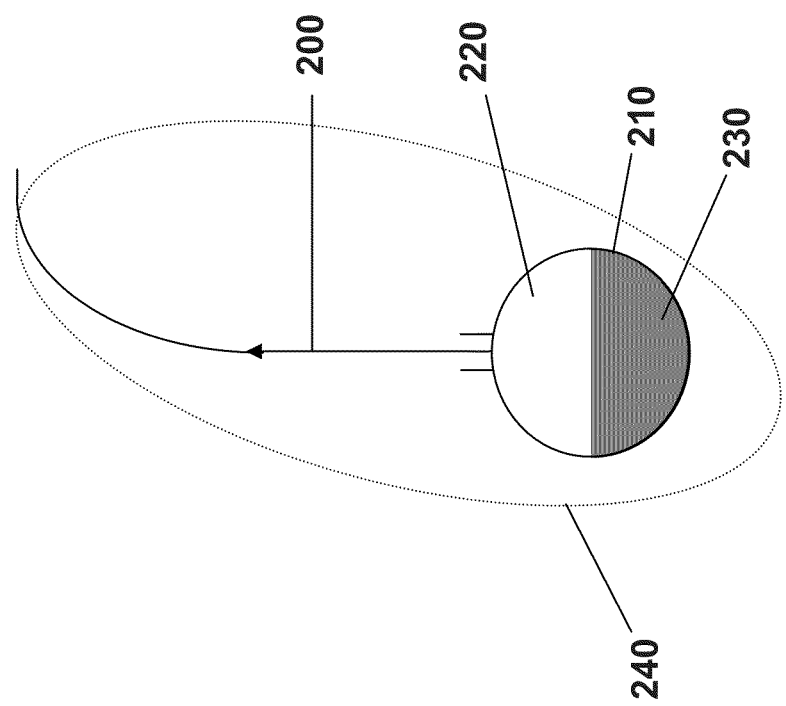
FIG. 2. is a diagram illustrating the $N_2O_4$ reservoir and critical flow restrictor.

$N_2O_4$ reservoir and critical flow restrictor: FIG. 2 is a diagram illustrating the $N_2O_4$ reservoir 210 and tube 200. The reservoir 210 can be spherical or nearly spherical or tubular. The reservoir 210 can be made from a material that is chemically stable against $N_2O_4$. Based on the chemical properties, the reservoir can be manufactured out of fused silica (a high grade of quartz), aluminium or stainless steel. The reservoir can be made from a non-reactive metal such as palladium, silver, platinum, gold, aluminium or stainless steel.

The spherical shape is not only the strongest physically, but with the tube protruding to the center, would allow for operation in any direction with the liquid level never in contact with the tube 200 itself, thereby preventing liquid from being expelled from the system. Other shapes including geometric shapes, tubular shapes, cube shapes can be used as determined by a person of skill in the art.

The reservoir 210 and the tube 200 need to be heated to provide the pressure to drive the $NO_2$ out of the reservoir. In one embodiment, the delivery system illustrated in FIGS. 1 and 2 can include a heating element for use in cold weather environs (e.g., less than approximately 5° C. or those temperatures in which the antioxidant-water combination would freeze and or the $N_2O_4$ would freeze). The heating element is associated with the reservoir. The heating element may be electrically, chemically, or solar powered. For example, the heating element can be a 20 watt heater which can be an Omega Stainless Steel Sheath Cartridge Heater. The system can also include a thermoelectric cooler so that the system can both be heated and cooled. Such devices are available commercially and provide the ability to rapidly change the temperature. Alternatively, the reservoir or delivery system can be strapped or otherwise held close to an individual's body in order to utilize the individual's body heat to keep the system at operating temperatures (i.e., those temperatures that where $NO_2$ has sufficient vapour pressure and ascorbic acid-water remains a liquid), and to ensure that the dose of NO is adequate.

At 21° C., the pressure in the reservoir 210 would be equal to atmospheric pressure since the $N_2O_4$ (reference 230 in FIG. 2, boils at this temperature). At 30° C. the vapor pressure above the liquid would be equal to about 2 atmospheres. This increases to approximately 4 atmospheres at 40° C. and 8 atmospheres at 50° C. Pressures like this are sufficient to drive the vapor out of the storage vessel and through the tube 200 and into the air stream at the ribbed tube wherein $NO_2$ is converted into NO.

The pressure has been shown experimentally to approximately double every 10° C., which is expected from theory. Thus, to maintain a constant pressure and therefore a constant driving force, the temperature of the assembly 220 has to be controlled. A 1.0° C. rise in temperature would cause the pressure to increase by about 10% and therefore the concentration in the air stream to increase by 10%. In order to maintain a constant flow rate to within say +−5%, the temperature at the reservoir needs to be held constant to within 0.25° C.

One limitation on the amount of $N_2O_4$ that the reservoir 210 can contain is related to the consequences in the event of a catastrophic failure where all the liquid $N_2O_4$ suddenly escapes into the room and vaporizes to $NO_2$. If this were to ever happen, then the $NO_2$ level in the room should not exceed 5 ppm, which is the OSHA standard for the workplace. In a standard room defined in FDA Guidance document "Guidance Document for Premarket Notification Submissions for Nitric Oxide Delivery Apparatus, Nitric Oxide Analyzer and Nitrogen Dioxide Analyzer dated 24 Jan. 2000, a room is cited as 3.1×6.2×4.65 meter room, without air exchange. In order to meet this guideline, the maximum amount of $N_2O_4$ that can be contained in the reservoir would be about 1 gram, or 0.7 ml, which would last for about 4 days.

While the safety code was written for high pressure gas bottles where the pressure is typically greater than 2000 psi, it is much less likely to happen when the internal pressure is only 8 atmospheres, which is equivalent to only 112 psi. Indeed, high pressure gas bottles are considered empty when the pressure falls below 150 psi. Another approach for exceeding this limit, a storage vessel that can include a reservoir 210 and tube 200 can be surrounded with an alkaline solution 240 that can neutralize the acidic $N_2O_4$/$NO_2$ in case of a leak. In the event of a catastrophic rupture, the reservoir 210 can be designed to leak into the surrounding alkaline solution, thereby neutralizing the toxic $N_2O_4$. Alkaline solutions can be any solution with a pH higher than 7. Any alkaline solution can be used, including but not limited to calcium oxide (flaked lime), sodium hydroxide, sodium carbonate, potassium hydroxide, ammonium hydroxide, sodium silicate. The same alkaline solution can also be used to neutralize any residual $N_2O_4$ after use or if the system was discarded prematurely. In another example, activated charcoal can be used to absorb $NO_2$ and can be used in packaging.

In another embodiment, the $N_2O_4$ and the reservoir needs to be heated to about 50° C. or higher in order to stabilize the pressure in the storage vessel. A heating element can be used. The heating element may be electrically, chemically, or solar powered. In one embodiment, chemical energy from an exothermic reaction can be used to provide the heat. One compound which could provide this energy is powdered calcium oxide (CaO). When mixed with water it releases energy in the form of heat. This material is also the slaked lime that is used in concrete. It has also been packaged in a format to heat foodstuffs. The added advantage of this material is that it is also alkaline, and the same material can be used to neutralize the $N_2O_4/NO_2$ in the scenario described above.

Figure 3:
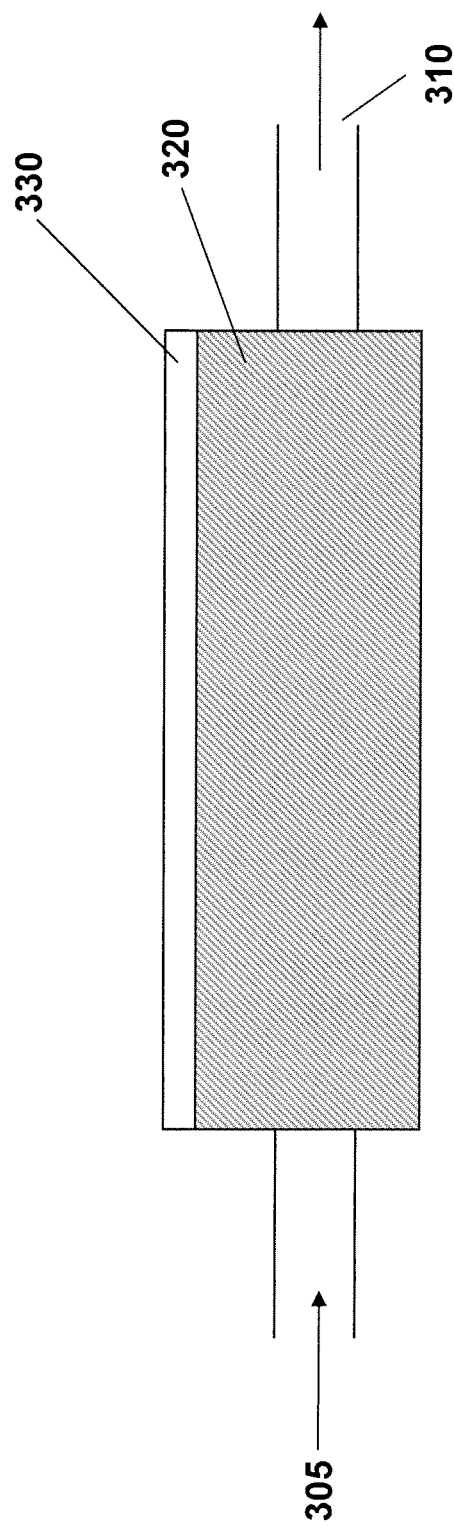
FIG. 3 is a diagram illustrating a standard NO generation cartridge.

Packed tube: In a general process for converting $NO_2$ to NO, an air flow having $NO_2$ is received by a standard NO generation cartridge through an inlet 305 and the air flow is fluidly communicated to an outlet 310 through the surface-active material 320 coated with the aqueous antioxidant as illustrated in FIG. 3. Typically, when a tube is packed with a powder, the powder tends to settle, much like a cereal box with corn flakes. Settling occurs due to vibration that is encountered during shipping, as well as during normal use. This is especially the case when the powder is fragile, like corn flakes, and cannot be well packed or when it is not possible to tightly compact the powder. For example, in packed columns for liquid chromatography, the powder is packed and used at great pressures; these columns are usually packed as a slurry to force the powder to be tightly packed. If the powder has an active surface material, such as silica gel, activated charcoal, activated carbon, activated alumina or desiccants such as calcium sulphate (DRIERITET™), to name just a few, and if it is desired to flow gas through the cartridge so that it comes into contact with the active surface, then the powder cannot be packed too tightly or the packed material can fracture, and allow gas to flow freely without creating too large of a pressure drop. In these cases, the technique that is used commercially today is to pack the powder and try and keep it tightly packed by means of a spring. In addition, the tubes have to be used vertically, so that as the powder settles, there will be no free gas path, which the gas can take to bypass the reactive bed, as shown in FIG. 3. If the tubes are not used vertically, then settling of the powder creates a channel 330, across the tube where the gas can flow preferentially. Creation of a channel negates the effect of the powder and renders the cartridge useless. This problem is so severe that a packed tube like this can only be used if the cartridge is vertical.

Figure 4:
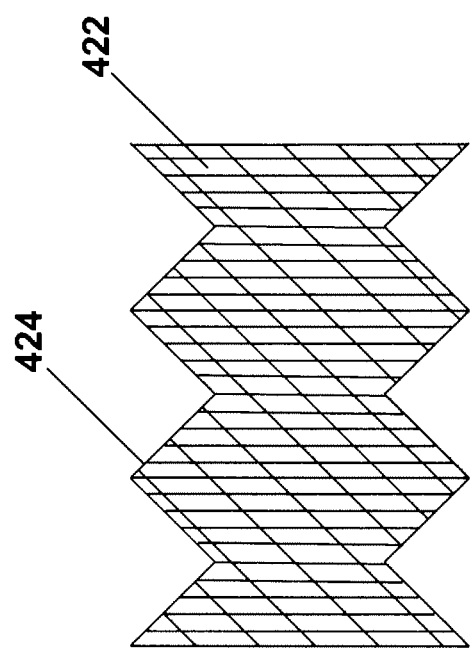
FIG. 4 is a diagram illustrating a tube with multiple concentric hollow ribs.
Figure 5:
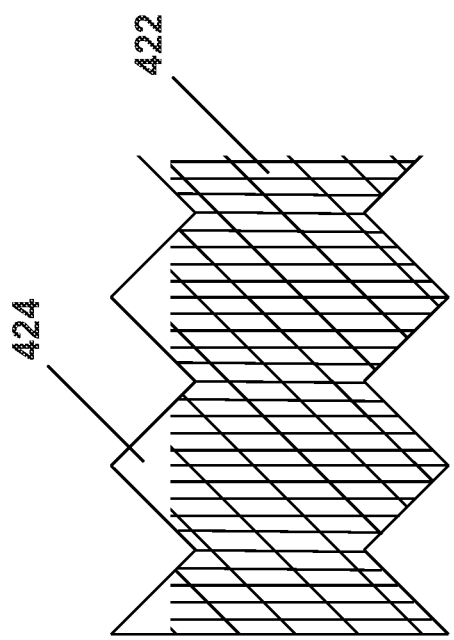
FIG. 5 is a diagram illustrating an expanded view of a tube with multiple concentric hollow ribs.
Figure 6:
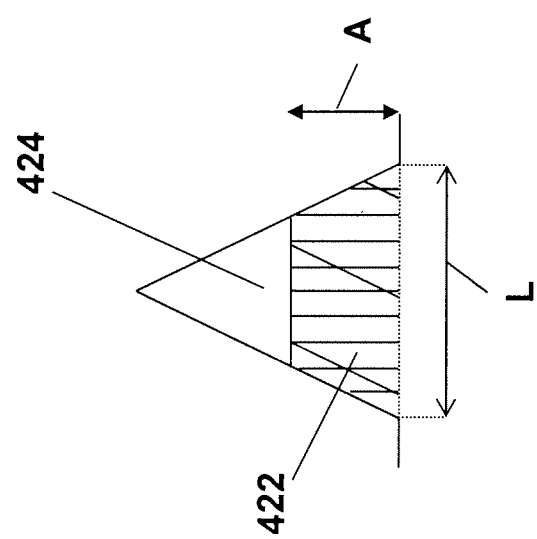
FIG. 6 is a diagram illustrating a rib.

FIG. 4-6 illustrates a tube with multiple concentric hollow ribs that overcomes this problem and allows for a powdered cartridge to be used at any angle, even after it has been exposed to severe vibrations. The tube can be used for all surface-active material including but not limited to silica gel, activated charcoal, or Drierite. The tube can be packed vertically and the powder, 422, is allowed to fill from the bottom to the top, also filling up all the volume enclosed by the ribs. If the tube were then vibrated and placed horizontally, the powder in the ribs would settle, as shown in 424. However, as long as the ribs are deep enough, the gas would not have a preferred channel. Gas flow would find the path to the settled volume more difficult than travelling though the powder bed.

FIG. 6 shows the close up detail of one of the ribs. For simplicity, the ribs are drawn as triangles, although in practice they can have rounded corners and a round top. L is the length at the base of the triangle, and A is the height of the powder above the base. As long as L is always less than 2 A, the preferred path for the air would be L, and not A. However, if the decrease in volume was so large that L was greater than 2 A, then the air channel in the rib would be the path of least resistance and the air would travel up into the channel, across the channel and down the other side to the next rib.

In one embodiment, the ribbed tube can be scaled up to be used in a packed bed reactor. At the present time powdered bed reactors are all situated vertically so as to avoid the problem. With the ribbed design, they can be situated at any angle, including horizontally.

EXAMPLE 1

The table below was generated with an air flow of 1 LPM air (using a mass flow controller), with an ascorbic acid/silica gel powder ribbed reactor. The $NO_2$ was supplied from a reservoir heated to 61° C. in a water bath. The NO reading is approximately 79 ppm. The fused quartz tube was 25 micron id and supplied by Restek as a "Guard column" ("GC"). The length of the GC column started at 39.88 inches. The GC column (except the last 2 inches) and liquid vessel are submerged in the water bath. Table 1 shows the relationship between length and concentration from this experiment.

TABLE 1

| Length [inches] | Concentration NO [ppm] | Calculated Concentration NO [ppm] | % Off | GC Tubing Removed [inches] | Temperature [C.] | Set Flow rate [LPM] |
| --- | --- | --- | --- | --- | --- | --- |
| 88.00 | 36.80 | NA | NA | | 61.8 | 1 |
| 76.50 | 41.95 | 42.33 | −0.91% | 11.5 | 621 | 1 |
| 64.25 | 50.33 | 50.40 | −0.14% | 12.25 | 61.4 | 1 |
| 50.00 | 63.80 | 64.77 | −1.52% | 14.25 | 61 | 1 |
| 39.88 | 79.00 | 81.21 | −2.80% | 10.125 | 61.3 | 1 |

The results show that within the limits of experimental error the output is inversely proportional to the length.

EXAMPLE 2

Figure 7:
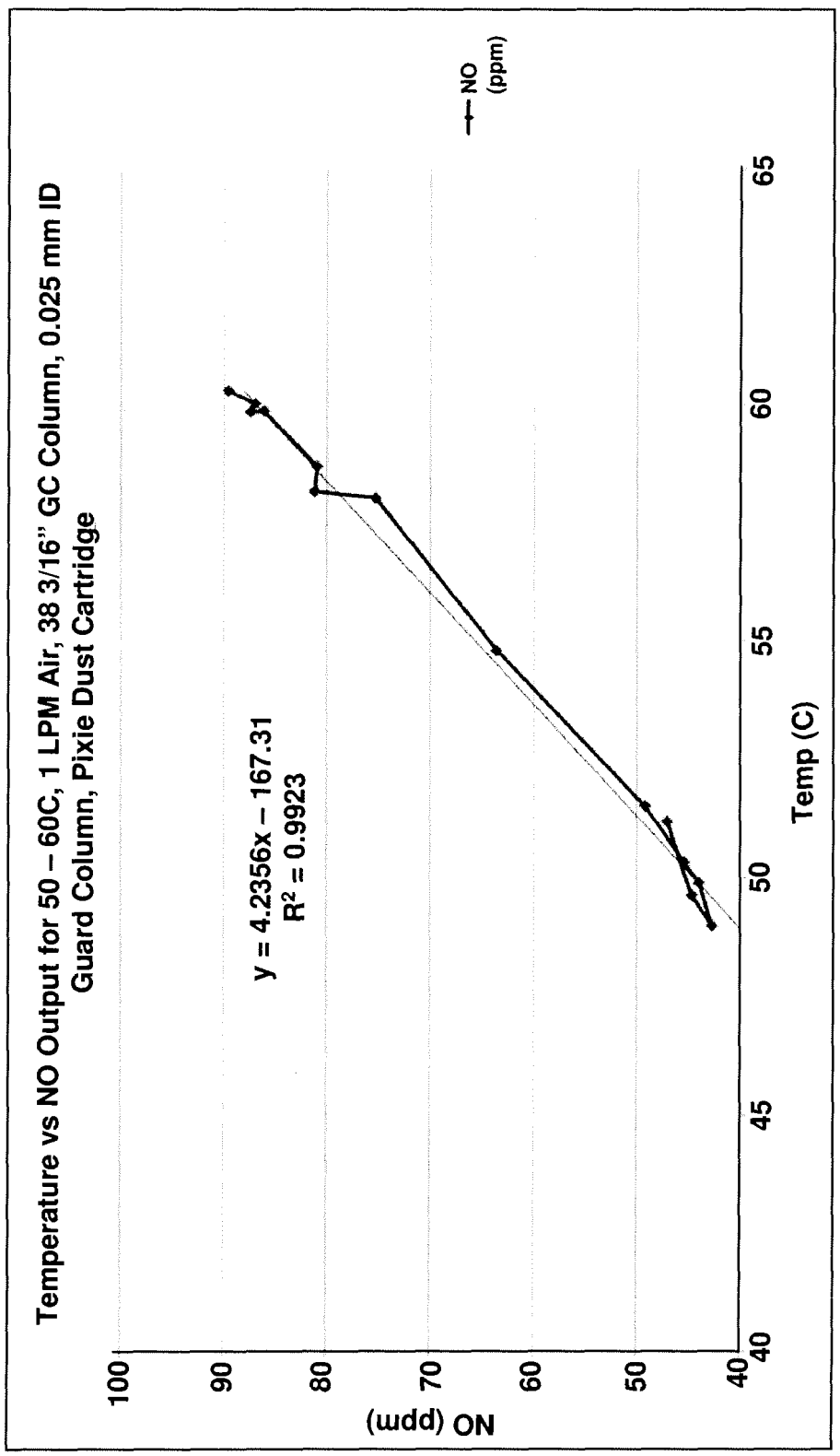
FIG. 7 is a graph illustrating temperature versus NO output for a 25 micron diameter ribbed tube packed with ascorbic acid/silica gel powder.

In this example, the length of the 25 micron diameter tube was held at 38 3/16 inches. The GeNOrator cartridge was a ribbed tube that was packed with the ascorbic acid/silica gel powder. The temperature of the storage vessel and the tube were varied from about 49° C. to just over 60° C. FIG. 7 demonstrates that over this temperature range, the increase in output was approximately linear, increasing 10-fold from 44 ppm at 50° C. to 88 ppm at 60° C.

EXAMPLE 3

Figure 8:
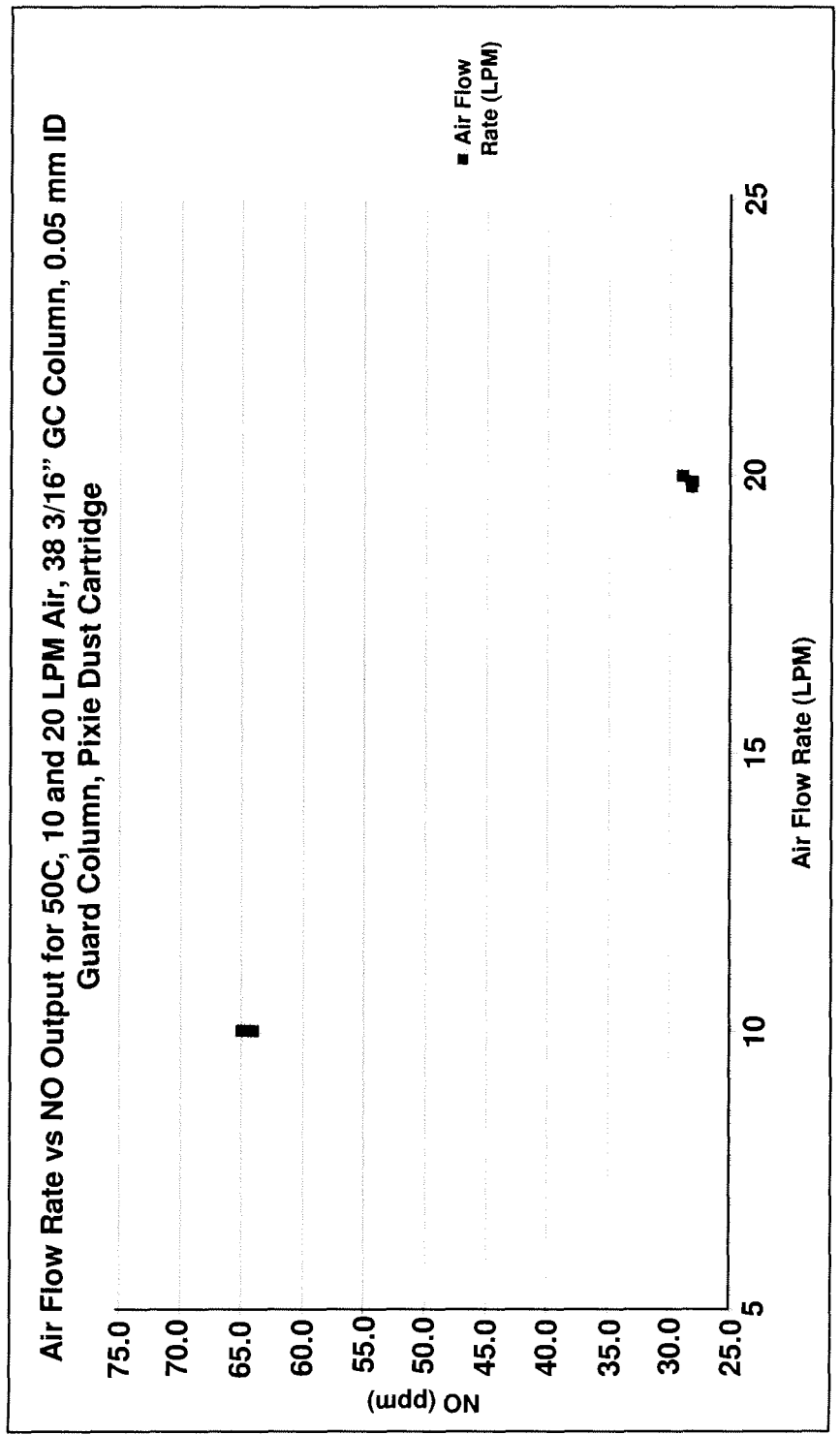
FIG. 8 is a graph illustrating air flow rate versus NO output for a 50 micron diameter ribbed tube packed with ascorbic acid/silica gel powder.

In this example a tube with a 50 micron id tube was used. The output of this tube was 64 ppm at 10 liter per minute and 28 ppm at 20 liters per minute; doubling the flow of air resulted in the output being halved, as expected. See FIG. 8. For this diameter, the expected output should vary with the $4^{th}$ power of the diameter as compared to a tube of 25 microns, or a factor of 16. From example 2, the output at 50° C. and 11 per minute was 44 ppm, which translates to an expected output of 70 ppm. This compares to the measured output of 65 ppm, which is within the limits of experimental error.

EXAMPLE 4

Figure 9:
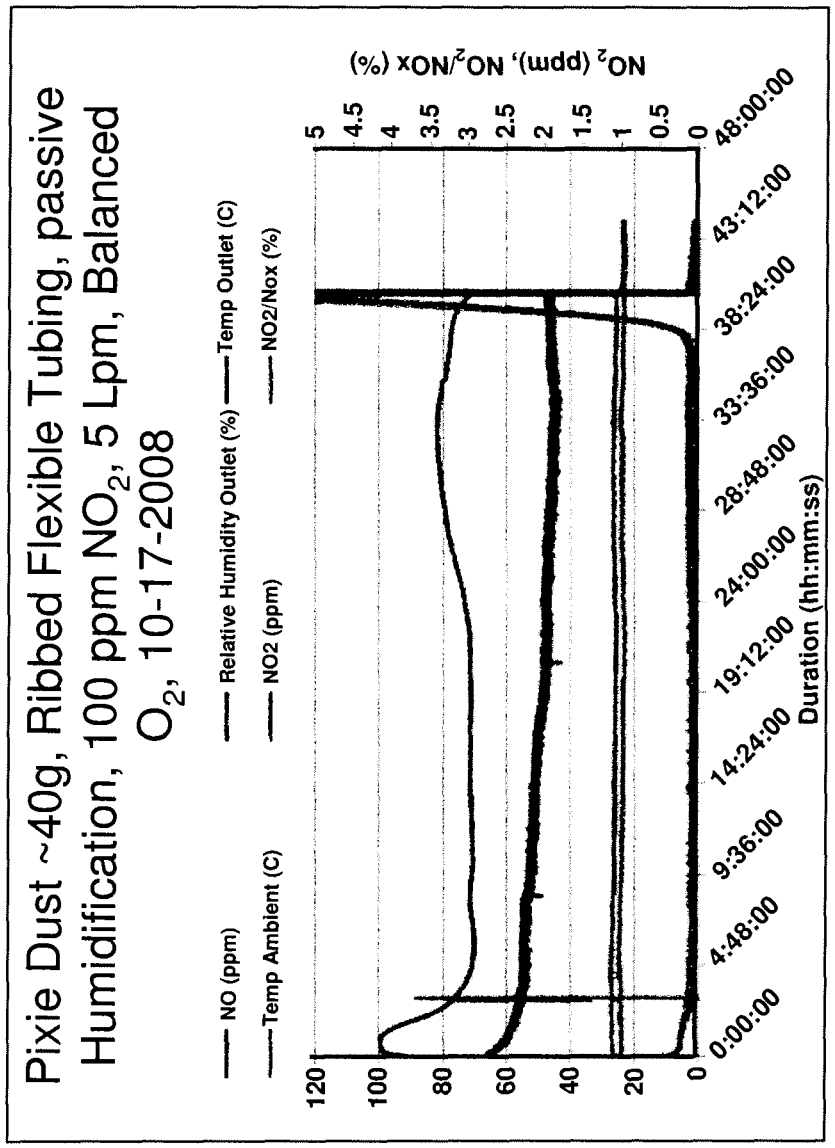
FIG. 9 is a graph illustrating NO and $NO_2$ output for a ribbed flexible tube. The graph further illustrates relative humidity, temperature at the outlet, ambient temperature and $NO_2/NOx$ ratios.

In this example, a ribbed flexible tubing was used. The rubbed tube was packed with 40 g of ascorbic acid/silica gel powder. 100 ppm of $NO_2$ was supplied in oxygen at 5 Lpm. The experiment was carried out over the course of approximately 42 hours as depicted in FIG. 9. FIG. 9 further illustrates that NO was released steadily for about 40 hours.

The various embodiments described above are provided by way of illustration only and should not be construed to limit the claimed invention. Those skilled in the art will readily recognize various modifications and changes that may be made to the claimed invention without following the example embodiments and applications illustrated and described herein, and without departing from the true spirit and scope of the claimed invention, which is set forth in the following claims.

What is claimed:

1. A system for delivering a therapeutic amount of nitric oxide, comprising:
    a liquid reservoir containing dinitrogen tetroxide;
    a tube coupled to the reservoir;
    a first ribbed tube coupled to the tube, wherein the first ribbed tube comprises:
    a plurality of hollow ribs,
    wherein each rib comprises a volume, a base and a length that is a distance across the base of the rib; and
    a surface-active material with a reducing agent, wherein a volume of the surface-active material is within each rib and a height of the surface-active material within each rib is a distance above the base of each rib the surface-active material extends into the rib, and wherein the length of each rib is less than twice the distance above the base of each rib the surface-active material extends into the rib, and the volume of each rib is greater than the volume of the surface-active material within each rib; and
    a patient interface coupled to the first ribbed tube, wherein the first ribbed tube is configured to convert nitrogen dioxide in a gas flow into nitric oxide prior to reaching the patient interface.

2. The system of claim 1, wherein the tube coupled to the reservoir is a quartz tube.

3. The system of claim 1, wherein the tube coupled to the reservoir is silica tube.

4. The system of claim 1, wherein the tube coupled to the reservoir has a bore size of about 50 microns.

5. The system of claim 1, wherein the tube coupled to the reservoir has a bore size of about 25 microns or less.

6. The system of claim 1, wherein the tube coupled to the reservoir has a bore size of 10 microns or less.

7. The system of claim 1, wherein the tube coupled to the reservoir is sealed before use.

8. The system of claim 1, further comprising an air pump in communication with the reservoir.

9. The system of claim 8, wherein the pump is a battery-driven pump.

10. The system of claim 1, wherein the patient interface is a mouth piece, nasal cannula, face mask, fully-sealed face mask or an endotracheal tube.

11. The system of claim 1, wherein the reservoir contains compressed nitrogen dioxide with or without a diluent gas.

12. The system of claim 1, wherein the reservoir further includes nitrogen, air, oxygen-enriched air, or substantially pure oxygen.

13. The system of claim 1, wherein the surface-active material is a silica gel.

14. The system of claim 1, further comprising a second ribbed tube coupled to the first ribbed tube, the second ribbed tube comprising a surface-active material and a reducing agent.

15. The system of claim 1, wherein the patient interface is a delivery tube adapted to deliver the gas flow to the patient's mouth or nose or an endotracheal tube attached to a ventilator or an anesthesia machine.

16. The system of claim 1, wherein the reservoir is spherical.

17. The system of claim 1, wherein the reservoir is a fused silica reservoir.

18. The system of claim 1, wherein the reservoir is a non-reactive metal reservoir.

19. The system of claim 18, wherein the non-reactive metal is palladium, silver, platinum, gold, aluminum or stainless steel.

20. The system of claim 18, wherein the reservoir is an aluminum reservoir.

21. The system of claim 18, wherein the reservoir is a stainless steel reservoir.

22. The system of claim 1, further comprising an insulation covering the reservoir and the tube coupled to the reservoir.

23. The system of claim 22, wherein the insulation covering further comprises an alkaline solution.

24. The system of claim 23, wherein the alkaline solution is calcium oxide, sodium hydroxide, sodium carbonate, potassium hydroxide, ammonium hydroxide, or sodium silicate.

25. The system of claim 1, wherein the gas is air or oxygen.

26. The system of claim 1, wherein the reducing agent is an antioxidant.

27. The system of claim 26, wherein the antioxidant is an aqueous solution of an antioxidant.

28. The system of claim 26, wherein the antioxidant is ascorbic acid, alpha tocopherol, or gamma tocopherol.

29. A device for delivering nitric oxide to a patient comprising:
    a liquid reservoir containing dinitrogen tetroxide;
    a tube coupled to the reservoir, wherein the tube coupled to the reservoir has a bore size of about 25 microns or less;
    a first ribbed tube coupled to the tube, the first ribbed tube comprising a surface-active material saturated with an aqueous solution of an antioxidant and a plurality of ribs, wherein the volume within each rib is greater than the a volume of the surface-active material within each rib
    a plurality of hollow ribs, wherein each rib comprises a volume, a base and a length that is a distance across the base of the rib; and
    a surface-active material saturated with an aqueous solution of an antioxidant, wherein a volume of the surface-active material is within each rib and a height of the surface-active material within each rib is a distance above the base of each rib the surface-active material extends into the rib, and the length of each rib is less than twice the distance above the base of each rib the surface-active material extends into the rib, and the volume of each rib is greater than the volume of the surface-active material within each rib; and
    a patient interface coupled to the first ribbed tube, wherein the first ribbed tube is configured to convert nitrogen dioxide in a gas flow into nitric oxide prior to reaching the patient interface.

30. The device of claim 29, comprising an air pump in communication with the reservoir.

31. The device of claim 29, wherein the pump is a battery-driven pump.

32. The device of claim 29, further comprising a nitrogen dioxide and/or a nitric oxide sensor.

33. The device of claim 32, wherein the nitrogen dioxide and/or nitric oxide sensor is calibrated automatically at periodic time intervals.

34. A ribbed tube comprising a body having a first end and a second end, wherein the body comprises
- multiple hollow concentric ribs, wherein each rib comprises a base and a length that is a distance across the base of the rib, and each rib comprises a volume; and
- a surface-active material, wherein a volume of the surface-active material is within each rib and a height of the surface-active material within each rib is a distance above the base of each rib the surface-active material extends into the rib, and wherein the length of each rib is less than twice the distance above the base of each rib the surface-active material extends into the rib, and the volume of each rib is greater than the volume of the surface-active material within each rib.

35. The tube of claim 34, wherein the surface-active material is saturated with an aqueous solution of an antioxidant.

36. The tube of claim 34, wherein the surface-active material comprises a silica gel, activated charcoal, activated carbon, activated alumina or calcium sulfate.

37. The tube of claim 34, further comprising a reducing agent.

38. The tube of claim 35, wherein the reducing agent is an antioxidant.

* * * * *